United States Patent [19]
Spears et al.

[11] Patent Number: 5,614,562
[45] Date of Patent: Mar. 25, 1997

[54] METHOD OF TREATING DRUG RESISTANT TUMOR CELLS USING ORGANOSELENONES

[75] Inventors: Colin P. Spears, Glendale, Calif.; Sang-Ihn Kang, Cranbury, N.J.

[73] Assignee: The University of Sourthern California, Los Angeles, Calif.

[21] Appl. No.: 991,482

[22] Filed: Dec. 16, 1992

Related U.S. Application Data

[63] Continuation-in-part of Ser. No. 675,614, Mar. 27, 1991, abandoned.

[51] Int. Cl.$^6$ .......................... A01N 29/02; A01N 29/04; A01N 29/12
[52] U.S. Cl. .......................... 514/744; 514/745; 514/747; 514/751; 514/762; 514/763; 514/764
[58] Field of Search .................................. 514/744, 745, 514/747, 751, 762, 763, 764

[56] References Cited

U.S. PATENT DOCUMENTS 4,617,189  10/1986  Stockel et al. .......................... 424/162
4,755,515  7/1988  Rabinovitz .............................. 514/255

OTHER PUBLICATIONS

Kang et al., "A Facile Synthesis of 2–and 3–Hydroxyalkylseleno Compounds", *J. Synth. Org. Chem.*, 2:133–135 (Feb., 1988).

Kang et al., "Linear Free Energy Relationships and Cytotoxicities of Para-Substituted 2-Haloethyl Aryl Selenides and Bis(2-chloroethyl) Selenides", *J. Med. Chem.* 30:597–602 (1987).

Spears, C. Paul, "Nucleophilic Selectivity Ratios of Model and Clinical Alkylating Agents by 4-(4'-Nitrobenzyl)pyridine Competition", *Mol. Pharm.* 19:496–504 (1980).

Kang et al., "Organoselenones Alkylation by Selenium–carbon Bond Cleavage" Abstract, *Proc. Amer. Assoc. Canc. Res.* 30:459 (Mar. 1989).

Kang et al., "Structure–Activity Studies on Organoselenium Alkylating Agents", *J. Pharm. Sci.* vol. 79, No. 1 (Jan. 1990).

Kang et al., "Phenyl Selenones: Alkyl Transfer by Selenium–Carbon Bond Cleavage", *J. Med. Chem.* 33:1544–1547 (1990).

*Primary Examiner*—Nathan M. Nutter
*Attorney, Agent, or Firm*—Robbins, Berliner & Carson, LLP

[57] ABSTRACT

Organoselenones of the formula $$R_1-Se(O_2)-(CH_2)_n-X$$

wherein $R_1$ is selected from the group consisting of aryl, vinyl, acetylenyl, and aralkyl, n is an integer equal to 2 to 6 and X is a leaving group selected from the group consisting of halides, sulfonates and selenones; were surprisingly found to be useful as alkylating agents which possessed a high degree of selectivity for nitrogen nucleophiles without the usual increased preference for sulfur nucleophiles. This property allows the effective use of these compounds as anti-cancer alkylating agents suitable for use in drug-resistant cell lines which display either thiol mediated drug resistance or MER(+)-mediated drug resistance. Two methods of synthesizing these compounds are also provided.

18 Claims, 2 Drawing Sheets

METHOD OF TREATING DRUG RESISTANT TUMOR CELLS USING ORGANOSELENONES

This invention was made with Government support under Grant No. 1RO1CA39629-03 awarded by the National Institutes of Health. The Government has certain rights in this invention.

This is a continuation-in-part of Ser. No. 07/675,614 filed Mar. 27, 1991, now abandoned.

BACKGROUND OF THE INVENTION

1. Field of the Invention

The present invention relates to the use of selenone compounds as anti-cancer agents, and to methods of making these compounds. Particularly, the present invention relates to the use of selenone compounds as anti-cancer alkylating agents against cell lines which display resistance to conventional anti-cancer alkylating agents.

2. Background

Classical alkylating agents may be defined as compounds that in protic media undergo aliphatic nucleophilic substitution reactions at saturated, $sp^3$-carbon electrophilic centers bearing an acidic leaving group. Discovery of the antitumor properties of mechlorethamine hydrochloride (nitrogen mustard) led to the synthesis of thousands of (2-haloethyl)imonium, aziridine, (2-haloethyl)sulfonium, and oxygen analogues by the early 1960's and to the development of alkylating agents as an established class of cancer chemotherapy agents. Platinating agents are also an established class of cancer chemotherapy agents. The ligand substitution reactions of platinating agents are essentially unimolecular in overall kinetics, and follow a very similar nucleophilic reactivity order. That is, in protic media (such as the biological intracellular situation), the second-order rate constants for nucleophilic substitution are in decreasing order: $S_2O_3^{2-}$—>$RS^-$—>$R_2N$~$N_3^-$—>$CH_3COO^-$—$Cl^-$—>$NO_3^-$—>$H_2O$. The range of values over this entire sequence is typically one-million fold or more. For classical alkylating agents and platinating agents, the anionoid electron pair of nitrogen is typically hundreds to tens of thousands times more reactive than hydrolysis with water.

The properties of nucleophilicity and electivity can be quantitatively expressed as n and s constants in the Swain-Scott linear free energy relationship. It has been shown that s and n constants of biological alkylating agents and nucleophiles, respectively, can be readily determined with high precision, using 4-(4-nitrobenzyl)pyridine (NBP) as a competitive substrate for alkyl product formation (Spears, C. P. Mol. Pharmacl.19:496–504,1981; Barbin,A.,Bereziat, A., O'Neill, I. K., and Bartsch, H. Chem.-Biol. Interact, 73:261–277, 1990; Kang, S. I., and Spears,C. P. J. Med. Chem. 33:1544–1547, 1990). Broad-spectrum antitumor alkylating agents show uniformly high s constants Spears, C. P. Mol.Pharmacol. 19:496–504, 1981; in contrast, mutagenically efficient alkylating agents show low values (Peterson, A. R., Landolph, J. R., Peterson, H., Spears, C. P., and Heidelberger, C. Cancer Res. 41:3095–3099, 1981; Barbin, A., and Bartsch, H. Mut. Res.215:95–106, 1989).

Extensive literature supports the hypothesis that alkylation at N7-guanine in DNA by ethyleneimines and platinating agents mediates the major cytotoxic effects of these agents. The basis for this high sensitivity for N7-G adduct formation (Brookes,P., and Lawley,P. D. Biochem. J.78:3923–3928, 1961) is the high nucleophilicity at N7-G (Pullman, A., and Pullman, B. Quart. Rev. Biophys. 14:289–380,1981) plus the unusually high selectivities of ethyleneimines and platinating agents for electron-rich nucleophiles (Spears,C. P. Mol. Pharmacol.19:496–504, 1981; Pearson, R. G., Sobel, H.., and Songstad, J. J. Am. Chem. Soc. 90:319–326, 1968; Ibne-Rasa, K. M. J. Chem. Educ. 44:89–94, 1967. Kreuger,J. H., Sudburg, B. A., and Blanchet, P. F. J. Am. Chem. Soc.96:5733–5736, 1974; Edwards, J. O. *Inorganic Reaction Mechanisms*. W. A. Benjamin, N.Y., 1965, pp. 51–89). Maxam-Gilbert DNA sequence analysis has shown that marked preferential attack occurs by ethyleneimines, generally at runs of guanines (Mattes, W. B., Hartley, J. A., and Kohn, K. W. Nucl. Acids Res. 14:2971–2987, 1986). These ethyleneimines include mechlorethamine, chlorambucil, and L-phenylalanine mustard. Studies have suggested 50-fold increases in reaction rates for native DNA over free deoxyguanosine (Price, C. C., Gaucher, M., Koneru, P., et al. Biochim. Biophys. Acta 166:327–359, 1968). This increase has been tied to the enhanced electrostatic potential at N7 by the presence of flanking guanines, and is not an effect of cross-linking (Gralla, J. D., Sasse-Dwight, S., and Poljak, L. G. Cancer Res. 47:5092–5096, 1987). Runs of guanines, such as the regulatory sequence, GGGCGG in SV40 DNA, may have an important role in oncogene expression. Recently, evidence has been presented that guanine-rich sequence preferences for alkylation by ethyleneimines occur in coding regions of c-myc and N-myc oncogenes. (Gralla, J. D., Sasse-Dwight, S., and Poljak, L. G. Cancer Res. 47:5092–5096, 1987; Futscher, B. W., and Erickson, L. C. Proc. Am. Assoc. Cancer Res. 29:468, 1988; Kallama, S., and Hemminki, K. Chem.-Biol. Interact. 57:85–96, 1986). Conceptual advantages of the use of platinating agents over classical alkylating agents include the narrow cross-linking distance of the biologically effective cis-compounds (3.4 Å), which is about one-half that of ethyleneimines. The other major difference is the occurrence of extremely high, calculable s constants of platinating agents. (Pearson, R. G., Sobel, H., and Songstad, J. J. Am. Chem. Soc. 90:319–326, 1968; Ibne-Rasa, K. M. J. Chem. Educ. 44:89–94, 1967. Kreuger, J. H., Sudburg, B. A., and Blanchet, P. F. J. Chem. Soc. 96:5733–5736, 1974; Edwards, J. O. *Inorganic Reaction Mechanisms*. W. A. Benjamin, N.Y., 1965, pp. 51–89). These differences could explain the ascendancy of platinating agents over ethyleneimines in the treatment of human ovarian cancer, germ cell neoplasms, and head and neck cancer, (DeVita, V. T., Jr., Hellman, S., and Rosenberg, S. A. (eds) *Cancer. Principles and Practice of Oncology*, 3rd Edition, 1989, pp. 495–503, 584–590, 657–705, 1084–1098, 1177–1196) despite the heavy metal toxicities.

Systematic chemical modifications of nitrosoureas and triazenes in the 1960s led to the discovery of 2-chloroethylating antitumor agents. These agents have desirably short cross-linking distances similar to those of platinating agents. This class of cross-linking agents includes BCNU (carmustine), CCNU (lomustine), and MeCCNU (semustine). (Schabel, F. M., Jr. Cancer Treat. Rep. 60:665–6, 1976). They are highly active in vivo against a broad range of murine neoplasms, but have demonstrated relatively narrow clinical activity. Clomesone and Cyclodisone, derivatives of sulfonates, are the most recent examples of bifunctional 2-chloroethyl derivatives (Gibson, N. W. Cancer Res. 49:154–157, 1989), currently under phase I clinical development.

In contrast to classical alkylating and platinating agents, the nitrosourea 2-chloroethylating agents react with DNA at a wide variety of nucleophilic sites (Barbin, A., and Bartsch, H. Mut. Res.215:95–106, 1989, Barbin, A., Bereziat, A., O'Neill, I. K., and Bartsch, H. Chem.-Biol. Interact. 73:261–277, 1990, Tong, W. P., Kohn, K. W., and Ludlum, D. B. Cancer Res. 42:4460–4464, 1982; Bartsch, H., Terracini, B., Malaveille, C., et al. Mut. Res. 110:181–219, 1983. Newbold, R. F., Warren, W., Medcalf, A. C. S., and Amos, J. Nature 283:596–599, 1980). In particular, significant product formation at the weakly nucleophilic O6-G site occurs. After 2-chloroethyl group transfer, cross-link formation may be intra- or inter-molecular at either the O6- or N7-G position. This further increases the plethora of products. A major chemical basis for the diverse product spread is the fact that nitrosoureas possess inherently low nucleophilic selectivities (Spears, C. P. Mol.Pharmacol. 19:496–504 1981; Peterson, A. R., Landolph, J. R., Peterson, H., Spears, C. P., and Heidelberger, C. Cancer Res. 41:3095–3099, 1981; Barbin, A., and Bartsch, H. Mut. Res. 215:95–106, 1989; Bartsch, H., Terracini, B., Malaveille, C., et al Mut.Res.110:181–219, 1983). On the other hand, it has been shown (by the inventors) that Clomesone, which may be therapeutically superior to nitrosourea 2-chloroethylating agents, has relatively high nucleophilic selectivity approaching that of chlorambucil (Kang, S. I., and Spears, C. P. J. Med. Chem. 33:1544–1547, 1990).

Problems exist with the use of prior alkylating agents, platinating agents and nitrosoureas as anti-cancer agents. Specifically, some cell lines demonstrate resistance to conventional alkylating agents, platinating agents and nitrosoureas.

As noted above, reaction at the O6-G site is a major mechanism of the cytotoxicity of nitrosoureas. A specific DNA repair enzyme, O6-G-alkyltransferase, can be induced to mediate resistance to this mechanism. Cells with increased levels of this enzyme are termed "MER(+)". Increased levels of this enzyme are associated with marked resistance to 2-chloroethylating agent cytotoxicity (Gibson, N. W. Cancer Res.49:154–157, 1989; Dolan, M. E., Pegg, A. E., Hora, N. K., and Erickson, L. C. Cancer Res. 48:3603–3606, 1988; Dolan, M. E., Norbeck, L., Clyde, C., Hora, N. K., et al. Carcinogenesis 10:1613–1619, 1989; A. E. Pegg, Cancer Res. 50:6119–6129, 1990). The occurrence of such enzymes in human cancers has been proposed as a mechanism for the surprisingly limited clinical antitumor activity of nitrosoureas when compared to their effectiveness in animal tumors. This resistance is a major problem with the clinical use of nitrosoureas (A. E. Pegg, Cancer Res. 50:6119–6129, 1990).

In contrast, the highly selective ethyleneimine and platinating agents are associated with, and induce drug resistance mediated by, a variety of intracellular thiol mechanisms. One such mechanism is elevation of intracellular reduced glutathione (GSH) to low millimolar concentrations. This is a common occurrence with high s constant nitrogen mustards and cis-diaminodichloroplatin (cisplatin or CDDP) (Dolan, M. E., Norbeck, L., Clyde, C., Hora, N. K., et al. Carcinogenesis 10:1613–1619, 1989; Ball, C. R., Connors, T. A., Double, J. A. Ujhazy, V., and Whisson, M. E. Int. J. Cancer 1:319–327, 1966; Dorr, R. T. Biochem. Biophys. Res. Commun.144:47–52, 1987; Kramer, R. A., Greene, K., Ahmed, S., and Vistica, D. T. Cancer Res. 47:1593–1597, 1987; Hamilton, T. C., Masuda, H., and Ozols, R. F. In: *Resistance to Antineoplastic Drugs* (Kessel, D., ed.), CRC Press, Boca Raton, Fla., 1989, pp.49–61). These alkylating agents with high s constants preferentially alkylate the sulfur atom of GSH, instead of forming the cytotoxic N7-G adduct. Drug resistance of this type may be overcome by various interventions, such as inhibition of glutathione reductase by buthionine sulfoxamine (Dorr, R. T. Biochem.Biophys.Res. Commun. 144:47–52, 1987; Kramer, R. A., Greene, K., Ahmed, S., and Vistica, D. T. Cancer Res. 47:1593–1597, 1987), which markedly depletes the levels of GSH.

Glutathione mechanisms and elevated levels of intracellular thiols can also strongly contribute to the resistance of cancer cells to doxorubicin and other antibiotic antitumor agents. Such resistance can also be reversed by thiol depletion treatment (buthionine sulfoxamine as described above) (Hamilton, T. C., Masuda, H., and Ozols, R. F. In: *Resistance to Antineoplastic Drugs* (Kessel, D., ed.), CRC Press, Boca Raton, Fla., 1989, pp.49–61).

Both enzymic and non-enzymic mechanisms for thiol-mediated drug resistance are known to occur in the presence of agents with high s constants. Thus, glutathione transferase activity can substantially contribute to the resistance of tumors to ethyleneimines and aziridines (Robson, C. N., Lewis, A. D., Wolf, C. R., et al. Cancer Res.47:6022–6027, 1987). In the case of cisplatin, metallotheinine, a thiol-rich peptide, can mediate resistance (Naganuma, A., Sakoh, M., and Imura, N. Cancer Res. 47:983–987, 1987).

In contrast to the case of high s constant alkylating agents, alkylating agents with low s-constants (such as the nitrosoureas which display only modestly greater reactivities for sulfur over nitrogen nucleophiles) rarely appear to suffer from resistance on the basis of a thiol mechanism (Aida, T., and Bodell, W. J. Cancer Res.47:1361–1366, 1987; Bedford, P., Walker, M. C., Sharma, H. L., et al. Chem. Biol. Interact. 61:1–15, 1987). As noted above, though, they suffer from MER(+) drug resistance.

Thus, it would be desirable to obtain cytotoxic compounds which possess high selectivity for N7-guanine yet avoid thiol-mediated mechanisms of resistance. High selectivity avoids MER(+)-mediated resistance. The present invention provides selenone compounds that satisfy these requirements.

Although the synthesis of bis(2-chloroethyl) selenide was first described in 1920, the antitumor potential of 2-haloethyl selenium compounds, as selenides, was not known until 1987. (Kang S. I. and Spears C. P., J. Med. Chem. 30:597–602, 1987). This was surprising, given the antitumor activities of inorganic selenium (Poirier, K. A., and Milner, J. A. J.Nutr. 113:2147–2154, 1983), the promising antitumor activity of selenium antimetabolite analogs, (Melvin, J. B., Haight, T. H., and Leduc, E. H. Cancer Res. 44:2794–2798, 1984), (Safayhi, H., Tiegs, G., and Wendel, A. Biochem. Pharmacol. 34:2691–2694, 1985), (Müller, A., Cadenas, E., Graf, P., and Sies, H. Biochem. Pharmacol. 33:3235–3239, 1984), the anticarcinogenic effect of dietary selenium (Shamberger, R. Mut. Res. 154: 29–48, 1985), which is an essential trace element (Buell, D. N. Semin.Oncol.10:311–321, 1983), the important role of selenium in glutathione metabolism (Chung, A. S., and Maines, M. D. Biochem. Pharmacol. 30:3217– 3223, 1981), and the requirement of some cancer cell lines in vitro for selenium as a nutrient (Carney, D. N., and De Leiji, L. Semin. Oncol. 15: 199–214, 1988).

The inventor's interest in 2-haloethyl selenium compounds derived from theoretical considerations of alkylating agent nucleophilic selectivity. High nucleophilic selectivity in an alkylating agent, as represented by the s constant of Swain and Scott, should display increased alkylation of N7-G in DNA and of other moderately strong intracellular nucleophilic sites.

A structural feature of alkylating agents which favors increased nucleophilic selectivity is high polarizability in the leaving group and of other atoms located near the reaction center (Bunnett, J. F. Annu.Rev.Phys.chem.14:271–290, 1963; Edwards, J. O., and Pearson, R. G. J. Am. Chem. Soc.84:16–24, 1962; Edwards, J. O. J. Am. Chem. Soc. 76:1540-, 1954; Edwards, J. O. *Inorganic Reaction Mechanisms*. W. A. Benjamin, N.Y., 1965, pp.51–89). Since nitrogen and sulfur atoms act in part as leaving groups in the final alkylation reactions of ethyleneimonium (Price, C. C., Gaucher, G. M., Koneru, P., et al. Ann. N.Y. Acad. Sci 163:593–600, 1969) and ethylenesulfonium ions, (Ingold, C. K. *Structure and Mechanism in Organic Chemistry*. Cornell Univ. Press, Ithaca, N.Y., 1953, pp. 384–385) selenium analogues were logical candidates for study because of the large, "soft" character of selenium (Ho, T.-L. Chem. Rev.75:1–20, 1975). In a report of s constant determination of model and clinical alkylating agents, the presence of an aromatic nucleus at the ethyleneimonium nitrogen also appeared to increase nucleophilic selectivity (Spears, C. P. Mol.Pharmacol.19:496–504, 1981). A comparison of reactivities, nucleophilic selectivities, and cytotoxicities of monofunctional 2-haloethylarylselenides was done with bifunctional aliphatic analogues (Kang, S. I., and Spears, C. P. J.Med.Chem. 30:597–602, 1987), (Kang, S. I., and Spears, C. P. J.Pharm.Sci. 79:57–62, 1990). It was found that 2-haloethyl selenides show a surprisingly wide range of values in reactivities, selectivities, and cytoxicities. Useful correlations between these values and Hammett constants were demonstrated. Some of the selenides were among the most reactive alkylating agents that have ever been described (making these potentially useful by topical application, intraarterial infusion, or intracavitary administration).

However, selenide alkylating agents suffer a number of drawbacks which appear to limit their clinical potential. The extremely high reactivities of the 2-chloroethyl selenides clearly is a problem for systemic intravenous therapy. The requirement for two selenium alkylating centers plus their generally poor aqueous solubilities discourage further preclinical development.

However, the selenides are useful as the immediate precursors for synthesis of 2-chloroethyl aryl selenones. The selenones of the present invention possess desirable solubilities and reactivities, short cross-linking distances, and show unusual and striking selectivities for N7-G type nucleophiles. The synthesis of monofunctional 2-chloroethyl arylselenides is carried out using diselenide or selenocyanate intermediates (Kang, S. I., and Spears, C. P. J. Med. Chem. 30:597–602, 1987). variation in alkyl chain length, halide leaving group, and bifunctionality (in terms of Se centers) can be achieved using hydroxyalkyl selenocyanate intermediates (Kang, S. I., and Spears, C. P. Synthesis 133–135, 1988; Kang, S. I., and Spears, C. P. J.Pharm. Sci.79:57–62, 1990).

Reich (*Organoselenium Chemistry*, J. Wiley & Sons, N.Y. 1987, p. 258) has commented that the chemistry of selenones has been little studied compared to sulfur analogues because harsh conditions for oxidation are required for synthesis, and because of the instabilities of selenoxides and selenones. Simple dialkyl selenones were synthesized from the corresponding dialkyl selenoxides by ozonation in a 1968 report (Paetzold, R., and Bochman, G. Z. Anorg. Allgem. Chem. 360:293-, 1968). Perhydrol treatment of the selenide was used later, to prepare selenacyclohexane-1,1-dioxide (Lambert, J. B., Mixan, C. E., and Johnson, D. H. J. Am. Chem. Soc. 95:4634–4639,1973). Peracetic acid and hydrogen peroxide have been useful to oxidize substituted diphenylselenides (or selenoxides) to the selenone analogs (Rebane, E. Chem.Scripta 5:65-, 1974; Bergman, J., Engman, L., and Siden, J. In: *The Chemistry of Organic Selenium and Tellurium Compounds,* Vol. 1. S. Patai and Z. Rappoport, eds., John Wiley and Sons, N.Y., 1986, pp. 546–558). Potassium permanganate has also been reported as useful for preparation of diphenyl selenones, but was unsuccessful for dimethylselenone from the selenide. A method which results in low yields for preparation of diphenyl selenones is direct selenonation of aromatic precursors with selenium trioxide, $SeO_3$. (Bergman, J., Engman, L., and Siden, J. In: *The Chemistry of Organic Selenium and Tellurium Compounds.* Vol. 1. S. Patai and Z. Rappoport, eds., John Wiley and Sons, N.Y., 1986, pp. 546–558).

The history of organoselenones ($R_1Se(O_2)R_2$) as a class has been reviewed. (Bergman, J., Engman, L., and Siden, J. In: *The Chemistry of Organic Selenium and Tellurium Compounds.* Vol. 1. (S. Patai and Z. Rappoport, eds.), John Wiley and Sons, N.Y., 1986, pp. 546–558.; Paulmier, C. *Selenium Reagents and Intermediates in Organic Synthesis.* Pergamon Press, N.Y., 1986, pp. 153–161; Reich, H. J. In: *Proceedings of the Fourth International Conference on the Organic Chemistry of Selenium and Tellurium* (F. J. Berry and W. R. McWhinnie, eds.), 1983, pp. 268–272. To date, no selenone compounds other than those of the present invention have been proposed as antitumor agents.

A variety of reactions are known to take place using organoselenones. Alkyl selenones of the type $PhSe(O_2)CH_2CHRCH_3$, where R=$CH_3$ or Ph, undergo syn-elimination reactions with heating (80°–100° C.) to produce olefins as well as products of reactions with benzeneseleninic and/or selenenic acid. The later side products are prevented from forming by the addition of 2-methoxypropene as a PhSeOH trap (Reich, H. J. In: *Organoselenium Chemistry* D. Liotta, ed., J. Wiley and Sons, Wiley Interscience, N.Y., 1987, p. 258). This type of selenone leaving group behavior has been used for synthesis of oxetanes, by treatment of selenones with NaOH in aqueous methanol (Shimizu, M., and Kuwajima, I. J. Org. Chem.45:4063–4065, 1980).

The alpha-protons of selenones are acidic, 2 $pK_a$ units more acidic than corresponding sulfones, which allows reaction by a α-selenonyl carbanion intermediate, as a second pathway, which is however infrequently observed (Reich, H. J. In: *Organoselenium Chemistry* D. Liotta, ed., J. Wiley and Sons Wiley Interscience, N.Y., 1987, p. 258).

A third leaving group reaction of organoselenones is that of facile SN2 displacement, originally mentioned by Reich who suggested that such behavior could make $PhSeO_2CH_3$ a biological alkylating agent (Reich, H. J. In: *Organoselenium Chemistry* (D. Liotta, ed.), J. Wiley and Sons (Wiley Interscience), N.Y., 1987, p. 258). Although $PhSeO_2CH_3$ was "three times as reactive as methyl iodide" (in methanol, 35° C.) in methylation of dimethylsulfide (to produce $(CH_3)_3S+$ and PhSe(=O)O), no rate data was provided. In addition, although nucleophiles such as alkoxides, cyanide, and amines were also mentioned to undergo similar SN2 displacements with $PhSeO_2CH_3$, no information on the nucleophilic reactivity order was provided.

Other evidence that organoselenones can undergo SN2 nucleophilic displacement (similar to reactions of the reactive intermediates of classical alkylating agents) has been very limited. $ArSeO_2CF_3$ was observed to undergo haloform-type decomposition under mildly basic conditions (OH—) to $HCF_3$ and $ArSe(=O)_2O$. The early preparation (J. Loevnich, et al., Ber. Dtsch Chem. Ges., Vol. 62, pp. 2856–2865, 1929) of 2-$NaphthSeO_2CH_3$ from 2-NaphthSeO$_2$Na and CH$_3$I is also probably an SN2-type reaction (in reverse) showing the high nucleophilicity of the aryl selenone leaving group. The latter reaction is suggested by the present inventors to represent an example of a general approach to synthesis of alkyl aryl selenones.

An additional reaction of selenones is that higher homologs of PhSeO$_2$R compounds (where R is aliphatic) at room temperature can undergo β-phenyl group migration reactions, probably through a carbocation mechanism, with a decrease in R-group ring size, acetal formation, among other reactions (Bergman, J., Engman, L., and Siden, J. In: *The Chemistry of Organic Selenium and Tellurium Compounds.* Vol. 1. (S. Patai and Z. Rappoport, eds.), John Wiley and Sons, N.Y., 1986, pp. 546–558.; Paulmier, C. *Selenium Reagents and Intermediates in Organic Synthesis.* Pergamon Press, N.Y., 1986, pp. 153–161.; Krief, A., Dumont, W., and De Mahieu, A. F. Tetrahed. Lett. 29:3269–3272, 1988).

The several types of leaving group behavior of the selenonyl group, together with the prior absence of any quantitative kinetic data, therefore, would not allow lead one skilled in the art to expect that 2-chloroethyl aryl selenones would be useful as alkylating agents analogous to clinical ethyleneimines and nitrosoureas.

In a preliminary report, in abstract form, (Kang, S. I., and Spears, C. P. Proc. Am. Assoc. Cancer Res. 30:459, 1989) the inventors described the NBP alkylating activities, reactivities, and in vitro cytotoxicities of several 2-chloroethyl aryl selenones against L1210/0, CCRF-CEM/0, SK-MES-1 and SK-LU-2 cells. This data did not include any drug-resistant cell lines nor was there any disclosure regarding the avoidance of drug resistance.

SUMMARY OF THE INVENTION

The present invention relates to use of organoselenones as anti-cancer agents and synthesis of these compounds.

One aspect of the present invention is the use of organoselenones as anti-cancer alkylating agents. In particular, the organoselenones are useful as anti-cancer alkylating agents against cell lines which ordinarily display resistance to alkylating agents. It was surprisingly found that these organoselenones, despite their high s values for nitrogen nucleophiles, are effective against cell lines which display drug resistance to other anti-cancer alkylating agents.

An additional aspect of the present invention is a method of synthesizing alkylselenones. The synthesis of these compounds is achieved from the corresponding alkyl selenides using meta-chloroperbenzoic acid (m-CPBA), or by nucleophilic substitution by ArylSe(=O)$_2$ Na in reaction with primary alkyl substrates.

DETAILED DESCRIPTION OF THE PREFERRED EMBODIMENTS

The present invention relates to organoselenones. In particular, the present invention relates to the use of selenones to treat cancerous cells, and to a method of forming the desired selenones using m-CPBA.

The organoselenones were found to have high nucleophilic selectivities (high s values) among nitrogen and oxygen nucleophiles, and were found to be surprisingly low in their selectivities toward sulfur nucleophiles. This combination of properties avoids two common drug resistance mechanisms, the MER(+) mechanism and the thiol-mediated mechanism.

The organoselenones of the present invention possess the following structure:

wherein R$_1$ is selected from the group consisting of alkyl, aryl, vinyl, acetylenyl, and aralkyl, n is an integer with a value of 2 to 6 and X is a leaving group selected from the group consisting of halides, sulfonates or a second selenone. The (CH$_2$)$_n$X group may be part of a cyclohexyl or larger group such as 2-azaadamayane and 1,3-diazaadamantane (e.g., Hane, J. T., and Henkel, J. G. Tetrahed. Lett. 31:2949–2952, 1990; Quast, H., and Muller, B. Chem. Ber. 113:2959, 1980). In particular, for purposes of the present invention the term "alkyl" refers to straight-chain or branched alkyl groups of 1 to about 20, preferably 1 to 6, carbon atoms, which groups are unsubstituted or may be substituted with one or more non-interfering groups as hereinafter defined. Cycloalkyl and heterocyclic groups containing, e.g., nitrogen and/or oxygen (comprising, e.g., 3 to about 10 ring atoms) are also contemplated as within the scope of the present invention. The term "aryl" refers to unsubstituted or substituted homoaromatic and heteroaromatic groups comprising single or multiple ring systems, in which the ring systems comprise about 5 to about 20 atoms, preferably 5 to about 14 atoms. Suitable homoaromatic groups include but are not limited to unsubstituted and substituted phenyl, naphthyl, anthryl and phenanthryl. Suitable heteroaromatic groups include but are not limited to unsubstituted or substituted thienyl, furyl, pyrrolyl, imidazolyl, pyridyl, pyrimidinyl, purinyl and quinolyl. Aryl groups in accordance with the present invention may similarly be substituted with one or more non-interfering groups. The terms "vinyl" and "acetylenyl" for purposes of the present invention are contemplated as including alkenyl of 2 to about 20 carbons and alkynyl of 2 to about 20 carbon atoms, respectively; preferably, the alkenyl or alkynyl groups will comprise 2 to about 6 carbon atoms and are unsubstituted or substituted by one or more non-interfering substituents. The term "aralkyl" refers to groups wherein the alkylene component comprises 1 to about 20 carbon atoms, preferably 1 to about 6 atoms, and an aryl group as hereinbefore defined; both the alkylene and the aryl components may optionally be substituted by one or more non-interfering substituents. The term "non-interfering substituents" for purposes of the present invention refers to substituents which do not react with the reagents (e.g., m-chloroperbenzoic acid) employed in the synthesis of the compounds from suitable starting materials and/or with other selenone molecules. Exemplary non-interfering substituents for purposes of the present invention include alkyl of 1 to about 20 carbon atoms (preferably, 1 to about 6 carbons), alkenyl of 2 to about 20 carbon atoms (preferably, 2 to about 6 carbons), alkynyl of 2 to about 20 carbon atoms (preferably, 2 to about 6 carbons), aryl, hydroxyl, alkoxy of 1 to about 20 carbon atoms (preferably, 1 to about 6 carbons), aryloxy (e.g., phenoxy), thioalkyl of 1 to about 20 carbon atoms (preferably, 1 to about 6 carbons), —CF$_3$, —OCF$_3$, —CHO, —COR' (wherein R' is alkyl, alkenyl, alkynyl or aryl as hereinbefore defined), —CO$_2$R' (wherein R' is as hereinbefore defined), —SOR' (wherein R' is as hereinbefore defined), —SO$_2$R' (wherein R' is as hereinbefore defined), —CN, —NO$_2$, —SO$_2$CF$_3$, NH$_2$, primary and secondary amino, —CONR"$_2$ (wherein each R" is independently selected from hydrogen, alkyl, alkenyl, alkynyl and aryl), NR"COR' (wherein R' and R" are as hereinbefore defined) and SO$_2$NR"$_2$ (wherein R" is as hereinbefore defined. Preferably, R$_1$ is an aryl group, n is 2 and X is chlorine. Most preferably, R$_1$ is a phenyl group or a p-methoxyphenyl group.

One method of synthesizing these compounds is a one-step process by treating the corresponding organoselenide with m-chloroperbenzoic acid (m-CPBA). Specifically, bifunctional alkylating target selenide compounds of general formula:

wherein R$_1$ is selected from the group consisting of alkyl, aryl, vinyl, acetylenyl, and aralkyl, n is an integer equal to 2 to 6 and X is a leaving group selected from the group consisting of halides, sulfonates and selenones, are treated with m-CPBA to form the desired selenone compounds. Preferably, R$_1$ is an aryl group, n is 2 and X is a halide. Most preferably, R, is a phenyl group or a p-methoxyphenyl group. It was surprisingly found that this reaction produced the desired organoselenones in good yields.

The foregoing reaction takes place using the following procedure. A solution is formed by dissolving in an organic solvent 2.5 to 4.0 molar equivalents of m-CPBA relative to the amount of selenide present in the reaction. The desired amount of selenide is dissolved in an organic solvent, and the solution of m-CPBA is added in a dropwise manner over a time period of 3 to 5 minutes.

After the reaction, the m-CPBA is neutralized by the addition of an inorganic base. The inorganic base serves to neutralize m-chlorobenzoic acid, a side product of the reaction. The organic layer is separated off using a separatory funnel, and the remaining aqueous layer is washed with an organic solvent to remove any trapped product. The combined organic layers are dried with sodium sulfate or other suitable drying agent, and concentrated. The resulting product can be purified by column chromatography on silica gel using an appropriate solvent system for the particular selenone. Determination of this solvent system is well within the skill of the art.

Preferred organic solvents for the m-CPBA solution include diethyl ether, dichloromethane, tetrahydrofuran, dioxane, toluene, acetone, and ethyl acetate. Preferred organic solvents for the solution of selenide are selected from dichloromethane, diethyl ether, and chloroform.

The reaction can be conducted within the temperature range 0° to 25° C. The preferred amount of time for the reaction to take place is 0.5 to 5.0 hours.

An alternative method of synthesizing these compounds is another one step process. A alkali metal salt of an organo seleninic acid is mixed with an alkyl halide and refluxed in a solvent. The reaction is quenched by adding water. The resulting product is isolated. (Loerenich, J., Freundling, H., and Fohr, M. Bes. Dtsch. Chem. Ges. 62:2856–2865, 1929).

The selenones of the present invention fulfill both criteria for effectiveness necessary for a class of antitumor alkylating agents. That is, they possess short cross-linking distance and high nucleophilic selectivity, that is, a highs constant for nitrogen nucleophiles relative to oxygen nucleophiles.

In particular, it was surprisingly found that the 2-chloroethyl aryl selenones displayed unexpected and surprisingly low reactivity toward sulfur relative to nitrogen nucleophiles. There has been no published indication of the potential usefulness of 2-chloroethyl aryl selenones against drug-resistant cancer cell types. The unusually low relative reactivities of 2-chloroethyl aryl selenones toward sulfur nucleophiles is unprecedented in the literature on primary alkylating agents and on platinating agents. That is, nucleophilic substitution reactions at saturated carbon, and ligand substitution reactions of platinating agents, have uniformly been characterized as showing markedly greater reactivities toward sulfur than nitrogen nucleophiles, typically about 100-fold greater, with no major significant deviation in this regard from the classic Swain-Scott-Ogston nucleophilic reactivity order (Ross, W. C. J. Adv. Cancer Res.1:397–449, 1953; Edwards, J. O., and Pearson, R. G. J.Am. Chem. Soc. 84:16–24, 1962; Spears, C. P. Mol. Pharmacol. 19;496–504, 1981; Ibne-Rasa, K. M. J. Chem. Educ. 44:89–94, 1967; Ogston, A. G., Holiday, E. R., Philpot, J. S. L., and Stocken, L. A. Trans. Faraday Soc. 44:45–52, 1948; Swain, C. G., and Scott, C. B. J. Am. Chem. Soc. 75:141–147, 1953; Wells, P. R. Chem.Rev.63:171–219, 1963; Osterman-Golkar, S., Ehrenherg, L., and Wachtmeister, C. A. Radiat. Botany 10:303–327, 1970; Barbin, A., Bereziat, A., O'Neill, I. K., and Bartsch, H. Chem.-Biol. Interact. 73:261–277, 1990; Koskikallio, J. Acta Chem. Scand. 23:1477–1489, 1969; Hartshorn, S. R. *Aliphatic Nucleophilic Substitution.* Cambridge University Press, 1973; Davis, R. E., Molnar, S. P., and Nehring, R. J. Am.Chem.Soc. 91:(Jan. 1), 1969).

This discovery that the organoselenones possess high nucleophilic selectivities and that they are more specific for nitrogen nucleophiles such as the pyridinyl nitrogen of NBP (an analog of N7-G in DNA) provides a key advantage to the present invention. This provides the surprising result that these compounds show much lower relative reactivities toward sulfur nucleophiles as compared to classical alkylating agents and platinating agents.

The present compounds provide the desired increase in aromatic (anionoid) nitrogen atom alkylation (such as N7-guanine in DNA), without the expected and unwanted increased thiol reactivity. Thus, the present invention, the use of 2-chloroethyl aryl selenones as anti-cancer agents successfully avoids multiple mechanisms of drug resistance such as the MER(+) phenotype, elevated GSH, and increased glutathione transferase levels. Yet, it achieves this combination while maintaining the desirable short cross-linking distance of the 2-chloroethyl group, and providing unprecedented selectivity for the pyridinyl nitrogen moiety.

All of the following cell lines would be expected to be relatively sensitive to organoselenone alkylating agents, on the basis of innate general alkylating agent sensitivity, or because of developed resistance to a specific alkylating agent (labeled). Mouse lymphocyte leukemias L1210/CPA, L1210/BCNU, L1210/L-PAM; WR (Walker 256 mustard-resistant) rat breast carcinoma; human ovarian OVCAR-3, 2780$^{CP}$, 2780$^{ME}$, 2780$^{AD}$; human leukemias CCRF-CEM, CCRF-SB, MOLT-4, RPMI 8226, K-562 are particularly sensitive; human colon COLO 320 DM and HT20 cells, LOX melanoma, non-small cell lung cancers SKLU 1, SKMES 1 and H23, breast cancer Hs578t, CNS tumor TE671 also show high levels of sensitivity (IC50 of about 1 µM or less). Tumors resistant to nitrosoureas on the basis of elevated O6-alkyl transferase enzyme activity (MER+) would also be expected to be sensitive.

The Examples are intended merely as guidance for one skilled in the art and not as limitations to the invention.

EXAMPLE 1

Synthesis of 2-Chloroethylphenyl Selenide 1.0 gm of phenyldiselenide was dissolved in 30 ml of ethanol at 0° C. 200 mg of $NaBH_4$ was added to the solution and the reaction was allowed to proceed until the yellow color of the solution disappeared. (If the yellow color does not disappear, then more $NaBH_4$ should be added to complete the reaction.) After the yellow color disappeared, 300 μl of $BrCH_2CH_2OH$ was dissolved in 3 ml of ethanol and was added dropwise to the reaction solution. After 30 minutes, another 300 μl of $BrCH_2CH_2OH$ was added. The solution was allowed to stir for 30 minutes. After the 30 minutes had ended, 1 ml of water was added to the reaction mixture and the solvent was removed on a rotary evaporator. The residue left in the flask was transferred to a separatory funnel using $CHCl_3$ and saline solution. The solution was extracted with $CHCl_3$ (20 ml×2), and the $CHCl_3$ layers were combined, dried with sodium sulfate, and concentrated by rotary evaporator. The resulting product was purified using column chromatography on silica gel with a 16:1 mixture of $CHCl_3$ to ethyl acetate as the eluent.

One gram of the resulting 2-hydroxyethyl phenyl selenide was dissolved in 15 ml of $CH_2Cl_2$. One ml of thionyl chloride was dissolved in 5 ml of $CH_2Cl_2$ and was added to the solution of the 2-hydroxyethyl phenyl selenide. The reaction mixture was refluxed for 1 h. The solvent was evaporated off and the remaining product transferred to a separatory funnel using $CHCl_3$. Twenty ml of water was added to the separatory funnel and was made weakly basic with 5% aqueous $NaHCO_3$. The $CHCl_3$ layer was removed from the separatory funnel, dried with sodium sulfate and removed from the product by rotary evaporation and then in vacuo.

EXAMPLE 2

Synthesis of 2-Chloroethyl Phenyl Selenone

The starting material, 2-choroethyl phenyl selenide, was synthesized, purified, and characterized as described in Example 1. To 1.0 g of 2-chloroethyl phenyl selenide in methylene chloride was added 3.0 g of m-chloroperbenzoic acid (m-CPBA) in methylene chloride. The reaction was carried out at 25° C. for 30 min, following which 1.5N NaOH was added slowly until the pH became slightly basic. The product, 2-chloroethyl phenyl selenone, was in the organic layer, which was extracted with $CHCl_3$, dried with $Na_2SO_4$ (anhydrous), and concentrated by rotary evaporator. Separation of 2-chloroethyl phenyl selenone from the major impurities, m-CPBA, m-chloro-benzoic acid, and PhSeSePh was done by silica gel chromatography with elution by methylene chloride:acetone (4:1). Unreacted 2-chloroethyl phenyl selenide and the diselenide(s) eluted early; 2-chloroethyl phenyl selenone eluted just prior to m-CPBA and m-benzoic acid. The migration of 2-chloroethyl phenyl selenone, which visualizes poorly on UV-fluorescent silica gel TLC, was followed by alkalinization of 1% NBP (in acetone)-reacted plates, which results in an intense purple color. Fractions containing only the 2-chloroethyl phenyl selenone were pooled, and solvent was removed under vacuum. The yield was 60–70% of the crystalline white product which has a m.p. of 65.5°–67.0° C.

EXAMPLE 3

Synthesis for Alkyl Aryl Selenones

Five grams of β-naphthelene seleninic acid, sodium salt, is mixed and refluxed with 3 gm of iodomethane in methanol. The reaction is quenched with addition of water, and the product extracted with ether. The ether is removed under vacuum, and the product taken up and recrystallized from ethanol. Methyl-naphthylene selenone is obtained as a golden yellow crystalline solid in 48% yield (3 gm), m.p. of 136°. This product is identical to material prepared by potassium permanganate oxidation of methyl-naphthylene selenide, and is not the methyl ester (which has a melting point of 106°).

EXAMPLE 4

Nucleophilic Selectivities of 2-Chloroethyl Aryl Selenones

Figure 1:
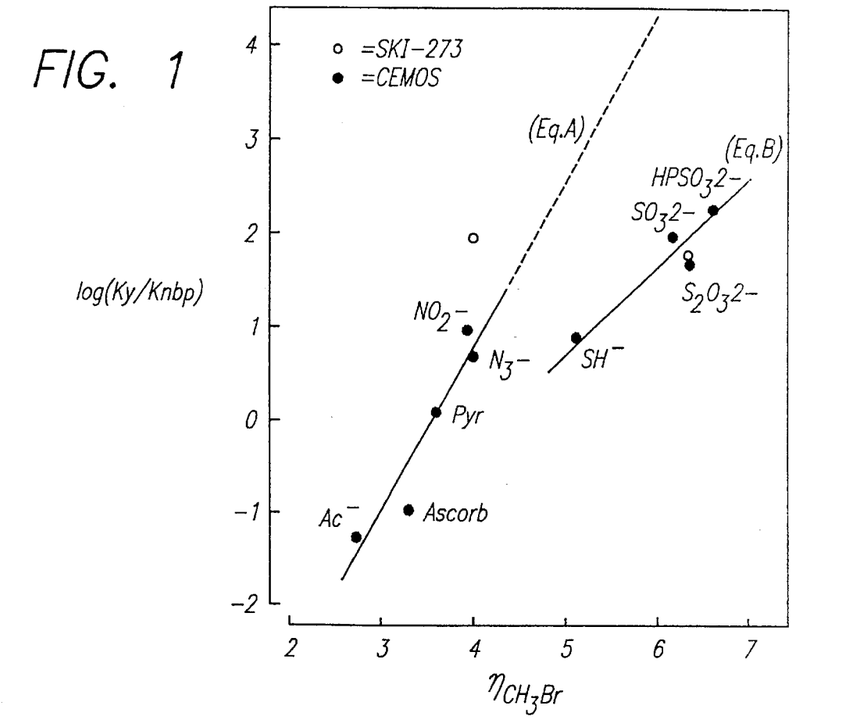
FIG. 1 shows product competition assays and nucleophilic selectivities of the organoselenone compounds.

FIG. 1 is a Swain-Scott plot of the ratio of second-order rate constants, log $(k_y/k_{nbp})$ for several model sulfur, nitrogen, and oxygen nucleophiles in their reactions with 2-chloroethyl 4-methoxy-phenyl selenone ("CEMOS"), vs. their published nucleophilicity $nCH_3Br$ constants. Values of n were taken to be 2.72 for acetate (AcO—), 3.3 for ascorbate, 3.6 for pyridine, 4.0 for azide ($N_3$), 3.94 for nitrite, 5.1 for thiol (SH), 6.18 for sulfite ($SO_3^{2-}$), 6.36 for thiosulfate ($S_2O_3^{2-}$), and 6.6 for thiophosphate ($HPSO_3^{2-}$) (derived from the Ogston "Competition Factor") (Ogston, A. G., Holiday, E. R., Philpot, J. S. L., and Stocken, L. A. Trans. Faraday Soc. 44:45–52, 1948).

In contrast to our previous experience and to that of the relatively sizable literature on aliphatic nucleophilic substitution at saturated carbon, the sulfur nucleophiles show unexpectedly low reactivities.

The slope of the linear regression equation through the 5 nitrogen and oxygen nucleophiles gives a Swain-Scott selectivity constant, s, equal to 1.79, by Eq. A, shown in FIG. 1:

$$\log (k_y/k_{nbp}) = 1.79 \; nCH_3Br - 6.40 \qquad \text{Eq. A}$$

This is the highest value ever found for saturated carbon, and is similar to values that can be calculated for platinating agents. The nearly zero value of log $(k_y/k_{nbp})$ at n=3.6 demonstrates (Spears, C. P. Mol. Pharmacol.19:496–504, 1981) the near equivalence of $nCH_3Br$ values of pyridine and NBP, and the absence of significant competing side reactions with solvent or Tris buffer. The intercept, 6.40, of Eq. A, confirms an extremely low susceptibility of CEMOS to aqueous hydrolysis.

Extrapolation of Eq. A predicts that the log $(k_y/k_{nbp})$ values for the thiol nucleophiles should have ranged from 3 to 5. However, the measured ratios of second-order rate constants were approximately 100-fold lower than this expectation. Also, the linear regression relationship, Eq. B (FIG. 1), for correlation of log $(k_y/k_{nbp})$ values vs. $nCH_3Br$ constants gave a sulfur nucleophile selectivity constant, s, equal to 0.84, approximately one-half of the value for reaction with nitrogen and oxygen nucleophiles:

$$\log (k_y/k_{nbp}) = 0.84 \; nCH_3Br - 3.40 \qquad \text{Eq. B}$$

Thus, in addition to low selectivity for thiols as a class, selectivity by CEMOS within the thiol series is also abnormally low. The downward deviation in log $(k_{S_2O_3}/k_{nbp})$ value, compared to nitrogen nucleophile selectivities including NBP alkylating activity, is an order of magnitude more extreme than many other primary carbon aliphatic agent described. Even in Koskikallio's study of methyl perchlorate (Koskikallio, J. Acta Chem. Scand. 23:1477–1489, 1969), in which oxygen, nitrogen, and sulfur nucleophiles had somewhat different slopes, the second-order rate constant for thiosulfate fell on each line (representing the intercept of the different slopes). Data confirmatory of the CEMOS observations were obtained with 2-chloroethyl phenyl selenone (SKI-273) are also shown in FIG. 1, and given in Table I. In this case, the selectivities for alkylation of $S_2O_3^{2-}$ vs. $N_3-$ were actually reversed, with log $(k_y/k_{nbp})$ values (mean±S.D.) of 1.77±0.05 and 1.95±0.11, respectively. This is a striking example, since $S_2O_3^{2-}$ (n=6.36) is normally 100-fold more reactive than $N_3-$ (n=4.0).

The alkylating activity of CEMOS in the FIG. 1 experiments was 103%, close to the value of 100% reported (Kang and Spears, J. Med.Chem. 33:1544–1547, 1990). The alkylating activity of KSI-273 was 140% relative to mechlorethamine HCl (=100%), and 170% relative to nor-nitrogen mustard. Thus, the high selectivities of 2-chloroethyl aryl selenones for aromatic nitrogen in aqueous, 37° C., neutral pH conditions is shown by both competition among classes of nucleophiles, and vs. solvolysis in aqueous acetone.

of 2-chloroethyl phenyl selenone, was 10 days in a separate experiment. In the experiments shown, i.p. drug was administered for 5 consecutive days, Days 1–5, beginning the day after tumor inoculation (on Day 0).

Mice were inoculated i.p. with $1 \times 10^6$ cells of P388 murine leukemia ascites passaged in BDF1 mice, in a volume of 0.1 ml. The selenones were formulated in normal (0.9%, w/v) NaCl for an injection volume of 0.3 ml. Control mice (12 in each group) received i.p. saline alone comparative examples 1 and 2. For each dose level and drug, 6 mice per group were used.

Figure 2A:
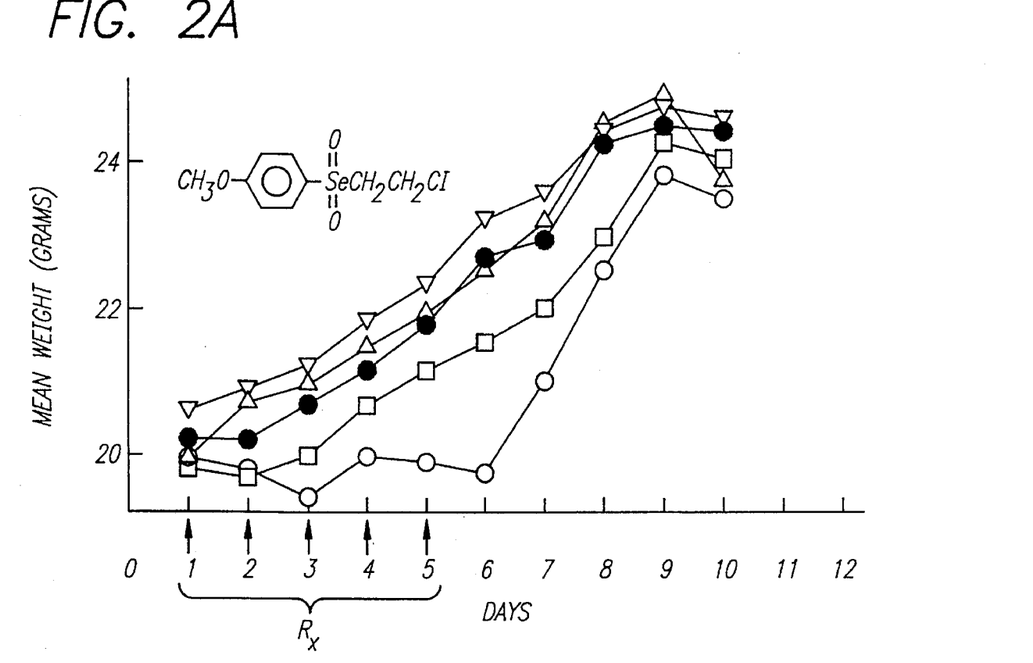
FIG. 2 shows the results of in vivo anti-tumor testing of 2-chloroethylaryl selenones in mice against murine P388 Leukemia ascites cells.
Figure 2B:
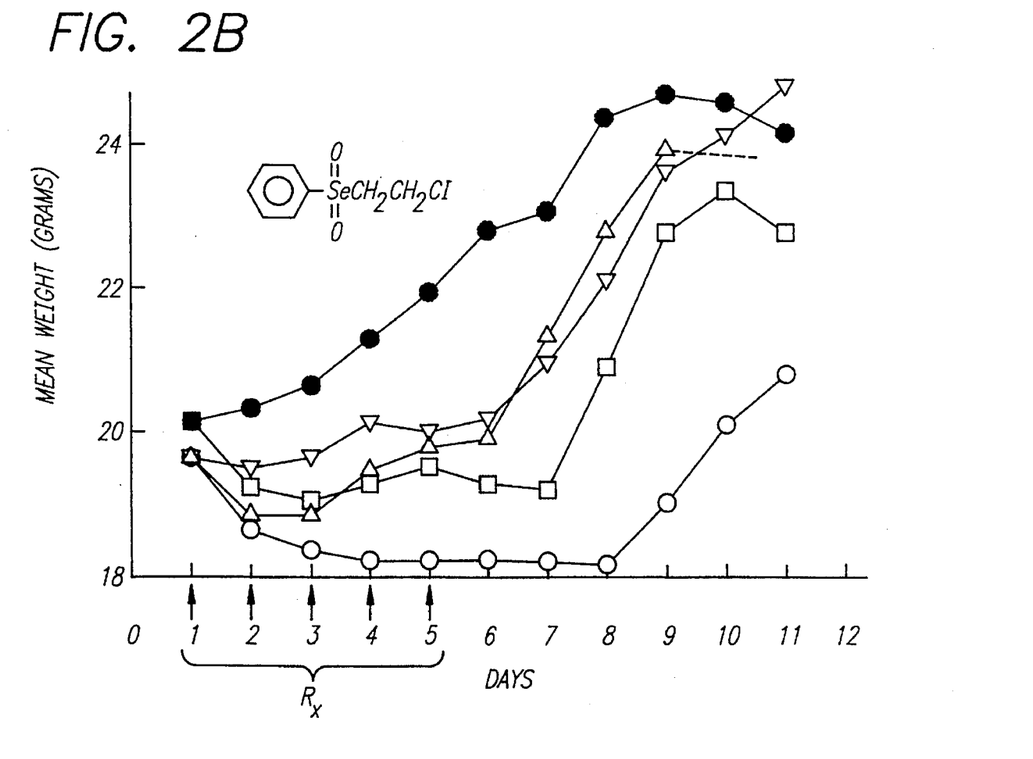

Control mice (filled circles) initially showed exponentially increasing weight gain, due to increasing burden of P388 tumor cells, which have a doubling time of 24 h or less and over a 90% growth fraction. The plateauing of weight increase, at Days 8–9, is consistent with classical Gompertizian tumor growth kinetics (Laird, A. K. Brit. J. Cancer 18:490–502, 1964). The delays observed in the time period before the onset of the exponential phase of weight increase are given in Table II, defined as the Growth Delay. FIG. 2A and Table IIA represent the results for the 2-chloroethyl 4-methoxy-phenyl selenone ("CEMOS") (examples 5–8), which appeared to be less effective than the parent 2-chloroethyl phenyl selenone compound (SKI-273) (FIG. 2B and Table IIB) (examples 9–12). Most notable in the latter was inhibition of tumor growth by the lowest dose of 2-chloro-

TABLE I

NUCLEOPHILIC SELECTIVITY RATIOS[a]
2-CHLOROETHYL PHENYL SELENONE vs. nor-NITROGEN MUSTARD

| COMPOUND | AA[b] | SECOND-ORDER RATE CONSTANT RATIOS | |
|---|---|---|---|
| | | $\log(k_S/k_{nbp})$ | $\log(k_N/k_{nbp})$ |
|  | 0.75 ± 0.004 | 1.77 ± 0.05 | 1.95 ± 0.11 |
| $ClCH_2CH_2NHCH_2CH_2Cl$ | 0.44 ± 0.010 (100%) | 2.63 ± 0.06 | 1.36 ± 0.07 |

[a]By competition between $S_2O_3^{2-}$ and NBP $\log(k_S/k_{nbp})$ or $N_3^-$ and NBP $\log(k_N/k_{nbp})$ at 37° C. and 10 h, in 52% aqueous acetone, using initial concentrations of 0.0435 mM and 0.0217 mM of 2-chloroethyl phenyl selenone and nor-nitrogen mustard, respectively, as described. Values, experimental means ± S.D.
[b]Alkylating activity, based on absorption at 560 nm of alkalinized alkyl-NBP. The selenone was assigned 1 alkylating equivalent/mol, based on the assumption that N-2-chloroethyl-NBP would not be expected to be significantly reactive.

EXAMPLES 5–12

In Vivo Growth Inhibition of P388 Leukemia

In FIG. 2 and Table II are shown the results of in vivo antitumor testing of 2-chloroethyl aryl selenones against murine P388 Leukemia ascites cells.

Examples 5–8 consisted of the use of 2-chloroethyl 4-methoxy-phenyl selenone to treat the mice. Examples 9–12 were the same as example 5 except 2-chloroethyl phenyl selenone was employed.

The doses of selenone given were below the acute intraperitoneal (i.p.) toxic dose, 20 mg/kg in either selenone, that resulted in ≧50% mortality within 2 hrs of injection; and were below 8 mg/kg, i.p., which was the single maximally tolerated dose (MTD) resulting in no acute deaths or shortening of lifespan. The maximally tolerated duration of the highest dose shown in FIG. 2 and Table II, 6 mg/kg/day i.p.

ethyl phenyl selenone tested (example 8), 1 mg/kg/d, which is one-eighth of the single dose MTD.

TABLE IIA

INHIBITION OF P388 ASCITES TUMOR GROWTH BY
2-CHLOROETHYL 4-METHOXY- PHENYL SELENONE

| | | I.P. DOSE, mg/kg | | GROWTH DELAY[a] |
|---|---|---|---|---|
| | SYMBOL | Daily | Total | (Days) |
| Comp Ex. 1 | • | 0 | 0 | |
| Ex. 5 | ▽ | 0.5 | 2.5 | 0 |
| Ex. 6 | △ | 1.0 | 5.0 | 0 |
| Ex. 7 | □ | 2.0 | 10.0 | 3 |
| Ex. 8 | ○ | 4.0 | 20.0 | 7 |

TABLE IIB

INHIBITION OF P388 ASCITES TUMOR GROWTH BY 2-CHLOROETHYL PHENYL SELENONE

| | | I.P. DOSE, mg/kg | | GROWTH DELAY[a] |
|---|---|---|---|---|
| | SYMBOL | Daily | Total | (Days) |
| Comp Ex. 2 | ● | 0 | 0 | |
| Ex. 9 | ▽ | 1 | 5 | 4 |
| Ex. 10 | △ | 2 | 10 | 7 |
| Ex. 11 | □ | 4 | 20 | 8 |
| Ex. 12 | ○ | 6 | 30 | 11 |

[a]Calculated from Day at which weight first exceeded baseline (Day 0) weight.

TABLE III

| | | IC50 (μM) | | |
|---|---|---|---|---|
| Example | Compound | L1210/0 | L1210/L-PAM | Ratio[a] |
| Comp. Ex 3 | L-Phenylalanine Mustard (L-PAM) | 1.6 | 7.0 | 4.4 |
| Comp. Ex 4 | Mechlorethamine (HCl) | 0.25 | 2.2 | 8.8 |
| Comp. Ex 5 | Busulfan | 55 | 60 | 1.1 |
| | Selenides: | | | |
| Comp. Ex 6 | $(MsOCH_2CH_2CH_2)_2Se$ | 2.3 | 16 | 7.0 |
| Comp. Ex 7 | $PhSeCH_2CH_2CH_2OMs$ | 52 | 100 | 1.9 |
| Comp. Ex 8 | $(CH_3)_2NCSeCH_2CH_2Cl$ | 18 | 30 | 1.7 |
| Comp. Ex 9 | Lutidine Derivative[b] | 12 | 28 | 2.3 |
| | Selenones: | | | |
| Example 13 | 2-chloroethyl phenyl selenone | 0.55 | 0.51 | 0.9 |
| Example 14 | 2-chloroethyl 4-methoxy phenyl selenone | 0.36 | 0.36 | 0.9 |

[a]Ratio of IC50s
[b]2,6-Bis(3-methanesulfonylpropylseleno)lutidine

EXAMPLES 13 & 14

Sensitivity of Alkylating Agent-resistant Leukemia Cells to 2-Chloroethyl Aryl Selenones Murine L1210 leukemia cells sensitive (L1210/0) and resistant (L1210/L-PAM) to L-phenylalanine mustard were obtained that are adaptable to either in vitro or in vivo passage. The parent L1210/0 line is sensitive to cyclophosphamide and BCNU as well as L-PAM and thioTEPA; the L1210/L-PAM line shows substantial in vivo resistance to L-PAM and thioTEPA (4 log cell kill differential) and moderate resistance to cyclophosphamide (>2 log differential).

Table III summarizes the IC50 values of 48-hr exposure of L1210/0 and L1210/L-PAM cells to several examples of alkylating agents and selenium analogs (Comparative Examples 3–9 and Examples 13 & 14). Broad resistance of the L1210/L-PAM cell line is shown by the approximately 4-fold and 9-fold increases in IC50, compared to L1210/0, for L-PAM and mechlorethamine, respectively (Comparative Examples 3 and 4). This level of resistance to 48-h exposure of ethyleneimines is typical of many examples of ethyleneimine alkylating agent resistant cell lines. Among the selenides, bis(3-methanesulfonylpropyl)selenide $(MsOCH_2CH_2CH_2)_2Se$ showed a 7-fold increase in IC50 for L1210/L-PAM (Comparative Example 6). The other selenides tested in both cell lines showed evidence of primary resistance already present in the L1210/0 cells, so that little significance can be attached to the observation of just 2-fold increases in their IC50s (Comparative Examples 7–9).

In contrast to the case of selenide alkylating agents, which manifest cross-resistance, the two selenones surprisingly showed no cross-resistance, and maintained their low IC50s found for the parental L1210/0 cells. (Examples 13 and 14.)

The poor results for the selenides, Table III, are not surprising, in view of their alkylating mechanism by selenonium ion intermediates and the normal linear relationship found for these agents between oxygen, nitrogen, and sulfur nucleophiles.

EXAMPLE 15

Lack of Cross-resistance to MER(+) Cells

Figure 3:
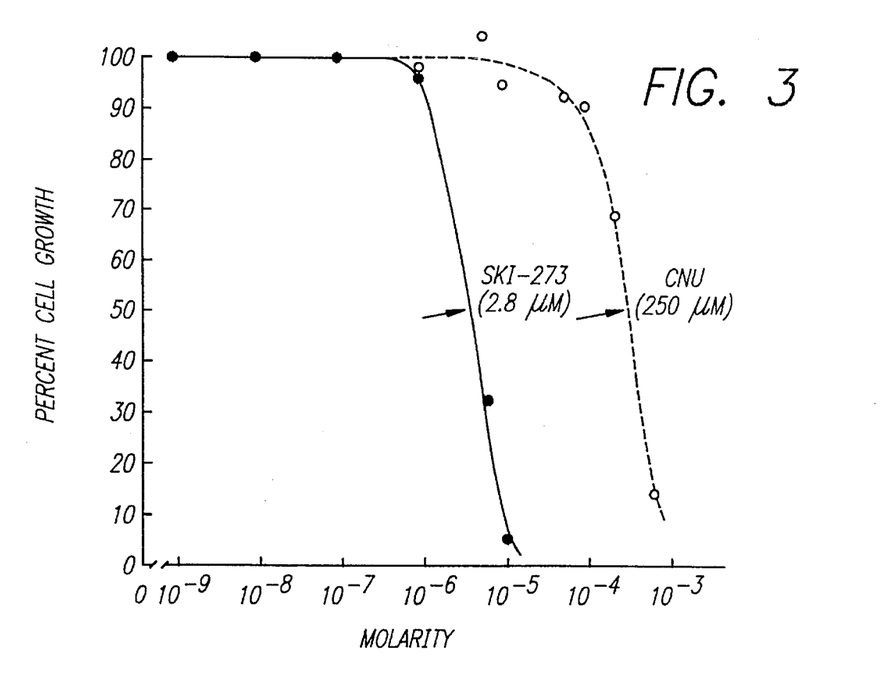
FIG. 3 shows the results of growth inhibition cytotoxicity assays of 2-chloroethyl 4-methoxyphenyl selenone against HT29 human colon carcinoma cells in vitro, comparison made to chloroethylnitrosourea.

FIG. 3 shows the results of growth inhibition assays of the cytotoxicity of 2-chloroethyl 4-methoxy-phenyl selenone against HT29 human colon carcinoma cells in vitro. (Example 15) These cells are very high in the alkyltransferase enzyme for repair of DNA guanine O6-alkyl products, and therefore are considered strongly MER(+) in phenotype. Levels of this enzyme in HT29 cells have averaged about 0.5 pmol/mg protein in recent studies (K. Chan, et al., unpublished). Evidence for the biologic importance of the MER(+) phenotype is demonstrated by the very high IC50 shown for chloroethylnitrosourea (CNU), 250 μM. (Comparative Example 10) IC50s of CNU in MER(−) cell lines are typically in the range of 12.5 to 50 μM. In marked contrast, the IC50 for 2-chloroethyl phenyl selenone (SKI-273)

against these HT29 cells was 2.8 μM, indistinguishable from the average IC50 (2.3±1.6 μM) reported for SKI-273 in an NCI in vitro screen for 7 different human colon carcinoma cell lines (Kang, S. I., and Spears, C. P. J. Med. Chem. 33:1544–1547, 1990). Thus, the lack of cross-resistance to ethyleneimines by the present invention of 2-chloroethyl aryl selenones is not associated with resistence mediated by by the alkyltransferase repair enzyme.

EXAMPLES 16–18

Sensitivity of Antibiotic-resistant Cancer Cells to 2-Chloroethyl Aryl Selenones Table IV shows data, provided by Bristol-Myers Laboratories, of in vitro IC50 testing of several selenium compounds against human colon carcinoma cells sensitive (HCT116) and resistant (HCT/VM46 and HCT/VP35) to two different antitumor antibiotics (both epipodophyllotoxin derivatives, VM26 and VP16). The data show comparisons of compounds of the present invention (Examples 16–18) with antitumor antibiotics and a lutidine-based selenide compound (Comparative Examples 11–13) in their cytotoxicity towards these cell lines.

Resistant cell line HCT/VM46 showed 4.9-fold and 3.2-fold increases in micromolar IC50s for VM-26 and VP-16 (Comparative Examples 12 and 13). More extreme was HCT/VP35, which manifested 15.1-fold and 10.0-fold increases in IC50s against VM26 and VP16.

The mechanism(s) of resistance of these cells to antitumor antibiotics is not known to the inventors, but the expectation is of the occurrence of the multiple drug resistant (MDR) phenotype, loss of Topoisomerase II activity, or loss of toxicity of Topoisomerase II-drug complexes, increased thiols, or some combination of these mechanisms. Cross-resistance to alkylating agents is regularly observed with cells showing resistance to VP16 or VM26.

However, in fact, the sensitivities of the antibiotic-resistant human colon cancer cells were found to be actually increased, over that of the parental antibiotic-sensitive line, for the 2-chloroethyl aryl selenones, about 2-fold more potent on average (Examples 16–18)

What is claimed is:

1. A method of treating drug resistant cancers comprising administering to a tumor-bearing animal an effective amount of a compound of formula:

$R_1$—Se($O_2$)—($CH_2$)$_n$—X wherein $R_1$ is selected from the group consisting of homoaromatic groups comprising single or multiple rings systems of 5 to 20 atoms, heteroaromatic groups comprising single or multiple ring systems of 5 to 20 atoms, alkenyl of 2 to 20 carbons, alkynyl of 2 to 20 carbon atoms, and aralkyl comprising an aryl component which is a homoaromatic group comprising a single or multiple ring systems of 5 to 20 atoms or a heteroaromatic group comprising a single or multiple ring systems of 5 to 20 atoms and an alkyl component comprising 1 to 20 carbon atoms, n is an integer equal to 2 to 6 and X is a leaving group selected from the group consisting of halides, sulfonates and selenones.

2. A method according to claim 1, wherein $R_1$ is a homoaromatic or heteroaromatic group, n is 2 and X is chloride.

3. A method according to claim 2, wherein $R_1$ is phenyl.

4. A method according to claim 2, wherein $R_1$ is p-methoxyphenyl.

5. A method according to claim 1, wherein the drug resistant cancel cells exhibit a thiol-mediated mechanism of drug resistance.

6. A method according to claim 1, wherein the drug resistant cancer cells possess MER(+) drug resistance.

7. A method according to claim 1, wherein the cancer cells are screened for resistance by exposure to classical alkylating agents.

8. A method according to claim 1, wherein the cancer cells are screened for resistance by exposure to agents which stimulate increases in intracellular thiols.

9. A method according to claim 1, wherein the cancer cells are screened for resistance by exposure to platinating agents.

10. A method according to claim 7, wherein the cancer cells are screened for resistance by exposure to nitrosourea alkylating agents.

11. A method according to claim 7, wherein the cancer cells are screened for resistance by exposure to clomesone and cyclodisone.

TABLE IV

ORGANOSELENONES: IN VITRO CYTOTOXICITIES AGAINST ANTIBIOTIC (MDR-TYPE)-RESISTANT CELLS

| | | | IC50 (μg/ml)[b] | | |
|---|---|---|---|---|---|
| Example | Compound | BMY #[a] | HCT116 | HCT/VM46 | HCT/VP35 |
| 16 | 2-chloroethyl phenyl selenone | 45127 | 1.02 | 0.44(0.4)[c] | 0.82(0.8) |
| 17 | 2-chloroethyl 4-methoxy-phenyl selenone | 45128 | 1.01 | 0.42(0.4) | 0.60(0.6) |
| 18 | 3-methanesulfonylpropyl phenyl selenone | 45129 | 6.34 | 4.93(0.8) | 5.15(0.8) |
| Comp. Ex. 11 | Seleno Lutidine derivative[d] | 45130 | >15.6 | >15.6 — | >15.6 — |
| Comp. Ex. 12 | VM-26 (Teniposide) | 26604 | 0.035 | 0.17(4.9) | 0.53(15.1) |
| Comp. Ex. 13 | VP-16 (Etoposide) | 26600 | 0.46 | 1.48(3.2) | 4.62(10.0) |

[a]Bristol-Myers accession number.
[b]Cell lines: HCT116 - human colon (sensitive to VP16 and VM26)
HCT/VM46 - human colon, VM26 resistant
HCT/VP35 - human colon, VP16 resistant
[c]Numbers in parenthesis: ratios of IC50 values (i.e., result divided by IC50 for HCT116).
[d]2,6-Bis(3-mesyloxypropylselene) lutidine 12. A method according to claim 10, wherein $R_1$ is a homoaromatic or heteroaromatic group, n is 2 and X is chloride.

13. A method according to claim 10, wherein $R_1$ is phenyl.

14. A method according to claim 10, wherein $R_1$ is p-methoxyphenyl.

15. A method of treating drug resistant cancers comprising administering to a tumor bearing animal an effective amount of 2-chloroethyl phenyl selenone.

16. A method according to claim 7, wherein the alkylating agent is selected from the group consisting of ethyleneimines and aziridines.

17. A method according to claim 8, wherein the agents which stimulate increases in intracellular thiols are selected from the group consisting of antitumor antibiotics and salts and organic derivatives of heavy metals.

18. A method according to claim 9, wherein the platinating agent is selected from the group consisting of cisplatin, carboplatinum and tetraplatinum.

* * * * *

UNITED STATES PATENT AND TRADEMARK OFFICE
CERTIFICATE OF CORRECTION

PATENT NO. : 5,614,562

DATED : March 25, 1997

INVENTOR(S) : Colin P. Spears and Sang-Ihn Kang

It is certified that error appears in the above-indentified patent and that said Letters Patent is hereby corrected as shown below:

Column 2, line 41, "P.F.J.Chem." should be --P.F.J. Am. Chem.--

Column 9, line 27, "R," should be --$R_1$--

Column 9, line 66, "highs" should be --high s--

Signed and Sealed this

Second Day of September, 1997

Attest:

BRUCE LEHMAN

*Attesting Officer*  *Commissioner of Patents and Trademarks*